(12) United States Patent
Decker et al.

(10) Patent No.: US 7,568,913 B2
(45) Date of Patent: Aug. 4, 2009

(54) OIL LAMP, AIR FRESHENER AND/OR FRAGRANCE RELEASE APPARATUS AND WICK THEREFOR

(75) Inventors: DayNa M. Decker, Studio City, CA (US); Steven Dodson, Kneeland, CA (US)

(73) Assignee: Lumetique, Inc., Los Angeles, CA (US)

( * ) Notice: Subject to any disclaimer, the term of this patent is extended or adjusted under 35 U.S.C. 154(b) by 559 days.

(21) Appl. No.: 10/760,117

(22) Filed: Jan. 15, 2004

(65) Prior Publication Data

US 2005/0037307 A1 Feb. 17, 2005

Related U.S. Application Data

(63) Continuation-in-part of application No. 10/300,649, filed on Nov. 19, 2002, now Pat. No. 6,991,453.

(60) Provisional application No. 60/331,904, filed on Nov. 19, 2001.

(51) Int. Cl.
*F23D 3/08* (2006.01)
*F23D 3/24* (2006.01)
*F23D 3/02* (2006.01)

(52) U.S. Cl. .................... 431/325; 431/298; 431/320

(58) Field of Classification Search .................... 431/12, 431/206, 188, 189, 325, 288, 289, 298, 320, 431/291; 422/125, 126; 126/43
See application file for complete search history.

(56) References Cited

U.S. PATENT DOCUMENTS

| | | | | |
|---|---|---|---|---|
| 2,976 A | * | 2/1843 | Terry | 431/206 |
| 5,936 A | * | 11/1848 | Chapin | 100/37 |
| 27,124 A | * | 2/1860 | Gutrie | 431/321 |
| 99,482 A | * | 2/1870 | Russel | 431/321 |
| 125,588 A | * | 4/1872 | Charles et al. | 431/321 |
| 147,386 A | * | 2/1874 | Gibson | 431/299 |
| 166,740 A | * | 8/1875 | Allen | 431/299 |
| 183,591 A | * | 10/1876 | Park | 431/206 |

(Continued)

FOREIGN PATENT DOCUMENTS

DE 42 42 509 * 6/1994

(Continued)

*Primary Examiner*—Carl D Price
(74) *Attorney, Agent, or Firm*—Law Office of David Hong (57) ABSTRACT

An oil lamp and fragrance release apparatus for providing a unique flame formation usable in a variety of decorative applications. The lamp includes a body that has an open upper end and that defines a chamber for carrying a combustible liquid. The lamp further includes a sheet wick having a lower end located in the chamber of the body, for contacting the combustible liquid, and an upper end projecting upwardly from the open upper end. The wick of inorganic material may be positioned between first and second plates arranged in a spaced, confronting relationship to enhance capillary action, may be freestanding stone of fibrous, permeable material or may be wrapped about a rigid plate. The wick provides a unique horizontal flame formation, while displaying décor on the outer surface of the flat wall. Optionally, the lamp may include scented oil and a conductive element to promote the release of fragrance upon heating, and the wick can be configured of material having high heat fragrance emanation.

13 Claims, 12 Drawing Sheets

U.S. PATENT DOCUMENTS

| | | | | |
|---|---|---|---|---|
| 388,862 | A | * | 6/1888 | Clarke ......................... 431/291 |
| 574,376 | A | * | 1/1897 | Baumer ....................... 431/291 |
| 594,517 | A | * | 11/1897 | Boughton ................... 431/206 |
| 736,545 | A | | 8/1903 | Quigley |
| 802,978 | A | * | 10/1905 | Duncan ....................... 431/206 |
| 862,027 | A | * | 7/1907 | Smith .......................... 431/206 |
| 967,162 | A | * | 8/1910 | Bladh .......................... 431/206 |
| 1,050,913 | A | * | 1/1913 | Bradfield .................... 431/206 |
| 1,190,219 | A | * | 7/1916 | Chadwick ................... 431/206 |
| 1,267,968 | A | * | 5/1918 | Bulle ........................... 431/291 |
| 2,080,251 | A | * | 5/1937 | Buskard ...................... 362/163 |
| 2,324,753 | A | * | 7/1943 | Alexiade .................... 431/323 |
| 2,324,783 | A | * | 7/1943 | Kronquest ................... 141/98 |
| 2,464,361 | A | | 3/1949 | Wilson |
| 2,758,460 | A | * | 8/1956 | Ciano .......................... 431/298 |
| 2,775,006 | A | * | 11/1956 | Kranc ......................... 422/125 |
| 3,162,030 | A | | 12/1964 | Irving |
| 3,321,938 | A | * | 5/1967 | Bureau ........................ 431/116 |
| 3,428,409 | A | | 2/1969 | Summers |
| 3,560,122 | A | | 2/1971 | Cassar |
| 3,759,478 | A | | 9/1973 | Schmitt |
| 3,998,922 | A | * | 12/1976 | Weiss .......................... 264/255 |
| 4,557,687 | A | * | 12/1985 | Schirneker .................. 431/291 |
| 4,690,484 | A | * | 9/1987 | Oba et al. ...................... 29/622 |
| 4,805,076 | A | | 2/1989 | Menter |
| 4,839,144 | A | * | 6/1989 | Martin ........................ 422/305 |
| 4,926,298 | A | * | 5/1990 | Zimmerman ................ 362/163 |
| 5,840,246 | A | | 11/1998 | Hammons |
| 5,911,955 | A | * | 6/1999 | Fullam ........................ 422/125 |
| 6,250,912 | B1 | | 6/2001 | Widdowson |
| 6,471,899 | B2 | | 10/2002 | Daiber |
| 6,562,294 | B1 | | 5/2003 | Smith |
| 6,667,006 | B2 | | 12/2003 | Richards |
| 6,823,780 | B2 | | 11/2004 | Vogt |
| 2002/0131888 | A1 | | 9/2002 | Zobele et al. |
| 2003/0036028 | A1 | | 2/2003 | Pesu |

FOREIGN PATENT DOCUMENTS

EP         1240907 A1    9/2002

* cited by examiner

OIL LAMP, AIR FRESHENER AND/OR FRAGRANCE RELEASE APPARATUS AND WICK THEREFOR

CROSS REFERENCE TO RELATED APPLICATIONS

This is a continuation-in-part of application Ser. No. 10/300,649 filed Nov. 19, 2002, now U.S. Pat. No. 6,991,453, which was issued on Jan. 31, 2006, which claims the benefit of U.S. Provisional Application No. 60/331,904, filed Nov. 19, 2001. The entire contents of both of these applications are hereby incorporated by reference.

BACKGROUND OF THE INVENTION

The present invention relates generally to devices of illumination and fragrance release, and more particularly, to oil lamps, air fresheners or fragrance release devices.

Oil lamps have long been used for decorative illumination and aromatic purposes. Oil lamps are typically made of glass or ceramic materials. Alternative materials such as, metal, plastics and wood could be used with advanced technologies. Such lamps typically include a body defining a chamber to hold a reservoir of combustible liquid and a wick to draw the liquid up through capillary action. The wick has an upper end extending out of an opening in the upper portion of the body and a lower end in contact with the reservoir of liquid. For effective capillary action, wicks typically are configured as a cord of fibers, such as cotton or fiberglass threads, braided in a rope-like configuration. When lit, the lamp forms a teardrop flame that is fed by the combustible liquid. Such lamps also may incorporate scented oil for aromatic purposes.

The wicks are round having a $\frac{1}{16}$-$\frac{1}{4}$ inch diameter for inside use and $\frac{1}{4}$ to one inch diameter for outdoor use. The flame height increases as the diameter increases. Oil lamps have the same regulations as candles, three inch inside. These woven wicks typically do not bend over, or create carbon heading. The fiberglass acts as a conductor.

The teardrop flame resulting from the wick's rope-like configuration can produce undesirable shadowing and otherwise limit decorative appeal. In addition, the release of fragrance in traditional lamps is tied to the wick's ability to conduct heat to the reservoir of scented oil; however, materials that promote capillary action, i.e., porous material, often are poor heat conductors. Thus, the release of fragrance is not optimal. To combat this, wicks often are provided with materials having a high heat conductivity, such as copper wiring, compromising capillary action.

Since wicks used for oil lamps or fragrance diffusers are made of woven or braided cotton or fiber materials, the wicks are extremely bendable. Therefore, a woven wick requires a wall or clamp around it to maintain straightness and central positioning. The wall may be glass, metal or ceramic. The oil lamp wicks are typically round in shape. They are either clamped to a top, outer device, where the wick loosely falls into the inner base of the lamp. This can affect the capillary flow of the fluid up the wick, causing undesirable or stable flame heights. Otherwise, a tunnel-like wall surrounds the wick but the wick is not tightly held allowing the wick to fall through the tunnel into the fluid to the inner base of the lamp or diffuser. This extinguishes the flame and depending on the size of the hole, the wick may be impossible to retrieve. The clamp or tunnel-like wall may make it difficult to replace the wick if needed depending on the design.

Typically, oil lamps have only a small hole where the single wick is inserted to fill the inner base of the lamp with oil. This can cause excessive spillage and/or additional tools, such as a funnel to safely fill the lamp may be needed. In addition, the wick may fall into the inner base, restricting easy retrieval thereof.

SUMMARY OF THE INVENTION

The present invention is directed to oil lamps and fragrance diffusers usable in a variety of decorative applications, providing a unique flame formation sustained by improve capillary action, and improved means for conducting heat into its scented oil reservoir for enhanced release of fragrance without the need of providing the wick with material having high heat conductivity.

Provided herein is an oil lamp having a unique flame formation usable in a variety of decorative applications. The lamp includes a body that has an open upper end and that defines a chamber for carrying a combustible liquid. The lamp further includes a sheet-sheet wick having a lower end located in the chamber of the body, for contacting the combustible liquid, and an upper end projecting upwardly from the open upper end. The wick may be positioned between first and second plates arranged in a spaced, confronting relationship to enhance capillary action and, when lit, the lamp provides a unique flame formation. Optionally, the lamp may include scented oil to promote the release of fragrance upon heating and the wick can be configured free of material having a high heat conductivity. High heat conductivity means the ability or power to conduct or transmit heat and the material does not melt, crack or shatter under high heat circumstances. A metal material is an example of a high heat conductor.

In a detailed aspect of an embodiment of the invention, the lamp further includes a plurality of clips to clamp the plates and the wick together. At least one of the clips may include a top portion extending above and curved over the upper portion of the wick so that the wick's flame heats the clip and a bottom portion positioned to contact the reservoir of liquid, thereby conducting heat from the flame into the reservoir.

A preferred embodiment includes interlocking exterior plates (not clamps) with the wick extending above the plates and the wick extending below the plates. The plates hold the wick tightly so that the wick does not fall through the plates and the wick maintains a stable wick height.

In another detailed aspect of a preferred embodiment of the invention, the plates are configured to hold wick such that the upper portion of the wick forms a selected decorative shape as viewed from above, such as line, arc, circle, square, triangle, heart or alpha-numeric shapes.

In another preferred embodiment, the wick is wrapped around a plate, made from aluminum, brass, glass, or steel, for example.

In a preferred embodiment a chamber to hold the fluid made out of polyethersulfone (PES) or other polymers, which have at least a V-0 rating from the UL-94 test, are good candidates. The chamber is designed to hold the wick upright, therefore allowing safe and easy filling of the fluid in the chamber. The polyethersulfone (PES) reduces the heat from coming in contact with alternative materials such as wood, metal or plastics.

An additional preferred embodiment includes a relatively hard, naturally formed mineral or petrified matter, such as sand or limestone. The high permeability matter conveys liquid by capillary action, allowing the oil to migrate upward towards the top portion of the matter releasing combustion of vapor, increases flame ionization or thermal conductivity. The matter can be in the shape of a circle, square, line, curve, triangle, heart, star, or alpha-numeric shapes, for example.

Additionally, the hard matter remains rigid, allowing it to stand alone without additional clip, plates or walls.

The woven fiber wicks can be combined with solidified minerals to maintain rigidity and consistent flame heights. The solidified minerals would be used in the place of external plates, rather they would be molded together.

The sheet-sheet wick whether woven or solid matter can be applied with oil or alcohol based products. A thicker wick is used with vegetable based oils, and a thinner wick is used with petroleum or alcohol based fluids.

Woven material may consist of fibrous material selected from a group consisting of woven roving fiberglass, mat fiberglass, undirectional fiberglass, bidirectional fiberglass, polyamide fibers, graphite fibers and polyethylene fibers.

The design of conventional oil lamp does not promote the dispersion of fragrance to the surrounding environment when the lamp is burning. This is due to the fact that the fragrance has no opportunity to be released from the fuel into the air during the operation of the lamp. The fragrance is almost completely consumed along with the fuel in the flame of the lamp as the oil lamp burns. Therefore, the addition of a fragrance to the fuel of a conventional oil lamp has been ineffective in producing a dispersion of fragrance into the surrounding air. Examples of fragrances are Lavender, Cedar, Cinnamon, Cypress, Evergreen, Gardenia, Green Apple, Honeysuckle, Jasmine, Lemon, Mulberry, Neutral, Ocean Breeze, Patchouli, Peppermint, Tangerine, Vanilla, Wild Peony, and Sandalwood; or they can be defined as, woody, floral, fruity, green etc.

Traditional oil lamp designs which have a single wick and are made from glass, do not release volatile elements into the air because the fuel is burned off by the flame. Therefore, in order to release a volatile element a heat conducting device must be added. The design of many of the oil lamps herein incorporate one or both materials; metal and ceramic which are known for emitting fragrance release with their permeable (e.g., ceramic or stone) or high heat conductivity (e.g., metal) qualities. Additionally, the type of fuel used will affect the fragrance or air purifying release. Alcohol will cause more vapors to be released therefore giving off more volatile elements compared to an oil-based product. It is an oil lamp with a fragrance release device or air purifier.

In other words, the air fresheners and fragrance release devices can apply to all the oil lamps that have the ceramic or metal plates or top. The metal heats the fragrances or air purifying fuel which then releases the scent or purifying agent into the air. The porous mineral material design will also assist in the fragrance or air purifying fuel release due to the permeably qualities combined with the heat from the flame. Examples of air purifying fuels are Neutral, Ocean Breeze, Lemon, Orange and Peppermint.

The fuel that is consumed by the lamp can be any burnable organic material which has at least one liquid component at ambient or room temperature. Typical fuels can include mineral oils, paraffin oils, aliphatic hydrocarbon oils, naphthenic hydrocarbon oils, kerosene, lower hydrocarbons, alcohols, vegetable oils, surfactants, fatty acids, triglycerides, glycerides, and ethers. Preferred fuels are mineral oils, triglycerides and vegetable oils. The fuel may contain colorants such as oil soluble dyes or other coloring agents to improve the appearance of the fuel. Such fuel can also include mineral salts which when burned produce a colored flame.

Suitable capillary tubes that can be employed as a fluid transfer means can be constructed of glass, metal, plastic, or any other materials that are compatible with the liquid fuel and volatile material and that will allow the movement of the liquid by capillary means. The preferred material of construction for the capillary tube is glass because of its availability, chemical resistance and aesthetics. The capillary transfer means can be integrated into the container as an integral part of the container or incorporated into the lamp as a separate element of construction.

Suitable porous inorganic materials that can be used as a fluid transfer means include ceramics, fritted glass, fiberglass, porcelain, stone, terra cotta, asbestos or other inorganic materials that contain reticulated openings or channels throughout the material's matrix. A preferred material of construction is fiberglass due to its ease of use, flexibility and high capacity to transfer a fuel and volatile material liquid.

Suitable porous organic materials that can be used as a liquid transfer means include cellulose materials, cotton, flax, linen, silk, paper, hemp, and wood. Because these materials have naturally occurring voids within their matrices, they are well suited to transfer liquids. A preferred porous organic material is cotton because of its economics and efficient transfer characteristics.

In summary disclosed herein are various designs for oil lamps, oil candles, fragrance diffusers and/or air fresheners. The woven wicks can be combined with solid minerals to maintain rigidity. The woven wicks can be roving fiberglass, mat fiberglass, unidirectional fiberglass, bidirectional fiberglass, polyamide fibers, graphite fibers and polyethylene fibers. Alternatively, solid mineral wicks such as sandstone and limestone, can be used. The wicks can be configured in many shapes and sizes and designed for safety. The wicks can be used as fragrance dispersers. They may be used with oil, alcohol or the like, as well as vegetable, animal or petroleum based liquids. Solid matter materials can be solidified minerals which are highly permeable. For fragrance dispersers, stone wicks can be used which release fragrance due to their high permeability. And for fragrance dispersers, metal or ceramic plates combined with woven wicks heat the fragranced oil releasing the scent into the air.

There are a number of safety design features for the lamps herein. For instance, a unique top is provided to cover the open fuel therefore keeping particles from polluting it; the lid is designed as a snuffer to eliminate the emission of soot and to safely extinguish the flame; the chamber is designed with brackets that hold the wick upright at all times; the chamber has air holes and barriers to materials that may become overheated thus maintaining safer temperature qualities of the base lamp; and the wick plates are designed to tightly clamp the wick into place so it does not fall through and extinguish or cause uneven flame heights.

Other features and advantages of the present invention should become apparent from the following description of the preferred embodiments, taken in conjunction with the accompanying drawings, which illustrate, by way of example, the principles of the present invention.

BRIEF DESCRIPTION OF THE DRAWINGS

Embodiments of the present invention will now be described, by way of example only, with reference to the following drawing figures.

DETAILED DESCRIPTION OF PREFERRED EMBODIMENTS OF THE INVENTION

Figure 1:
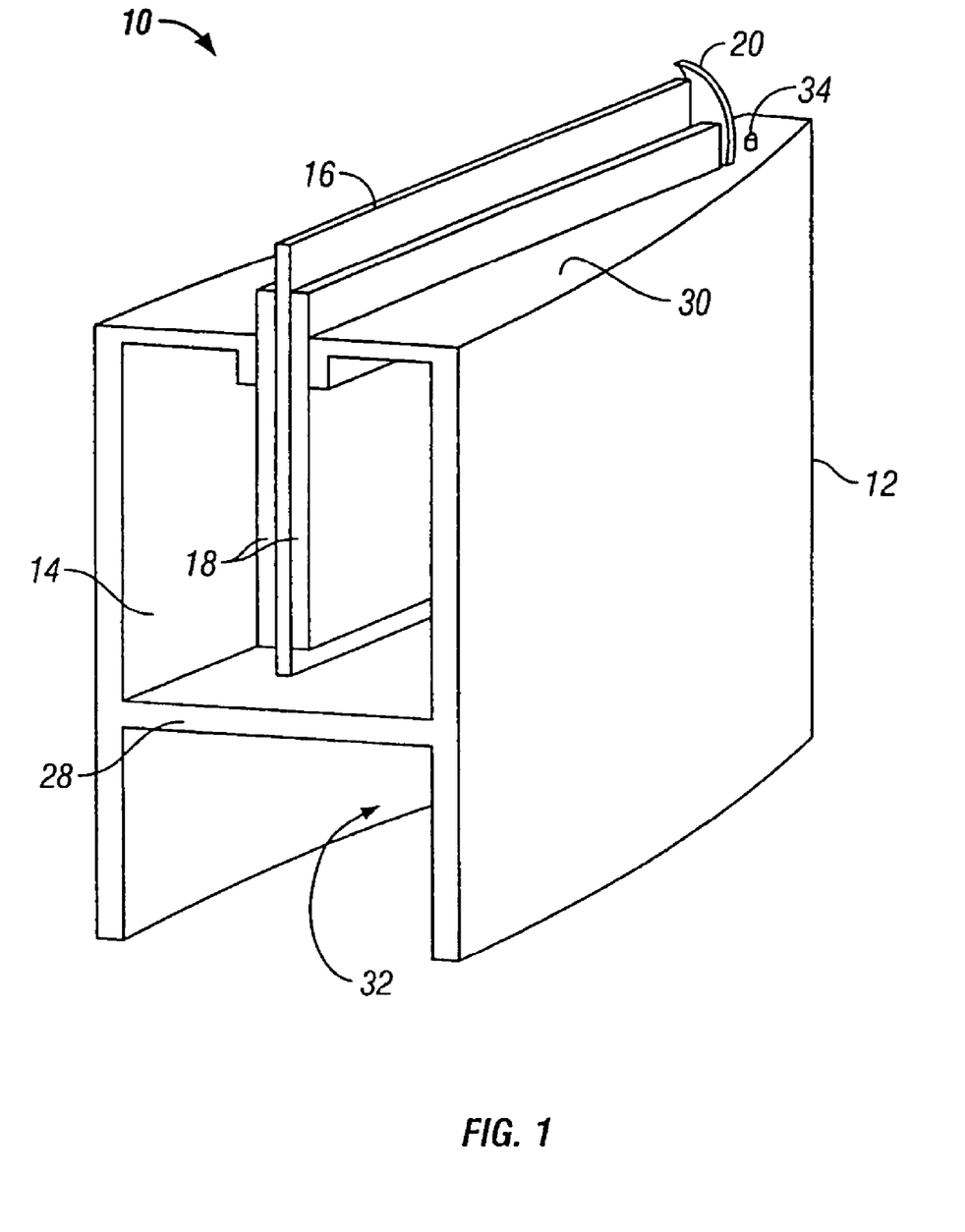
FIG. 1 is a cross-sectional perspective view of a preferred embodiment of an oil lamp in accordance with the present invention, the lamp having a body configured to hold an elongated wick.

With reference to the illustrative drawings, and particularly to FIG. 1, there is shown a lamp 10 having a body 12 that defines a chamber 14 to hold a combustible liquid and having a sheet wick 16. For purposes of this disclosure, the term lamp refers to a device that is configured to illuminate. The lamp includes two plates 18 extending into the chamber and configured to secure and press the wick, to promote capillary action of the liquid up the wick. When lit, the lamp provides a unique flame formation usable in a variety of decorative applications. The body further includes conductive elements, clips 20 (only one of which is shown), configured to secure the plates and conduct heat from the flame into the reservoir of liquid that, when used with scented oil, promote the release of fragrance. Moreover, the present invention makes it unnecessary to configure the wick with enhanced heat conductivity.

Figure 2:
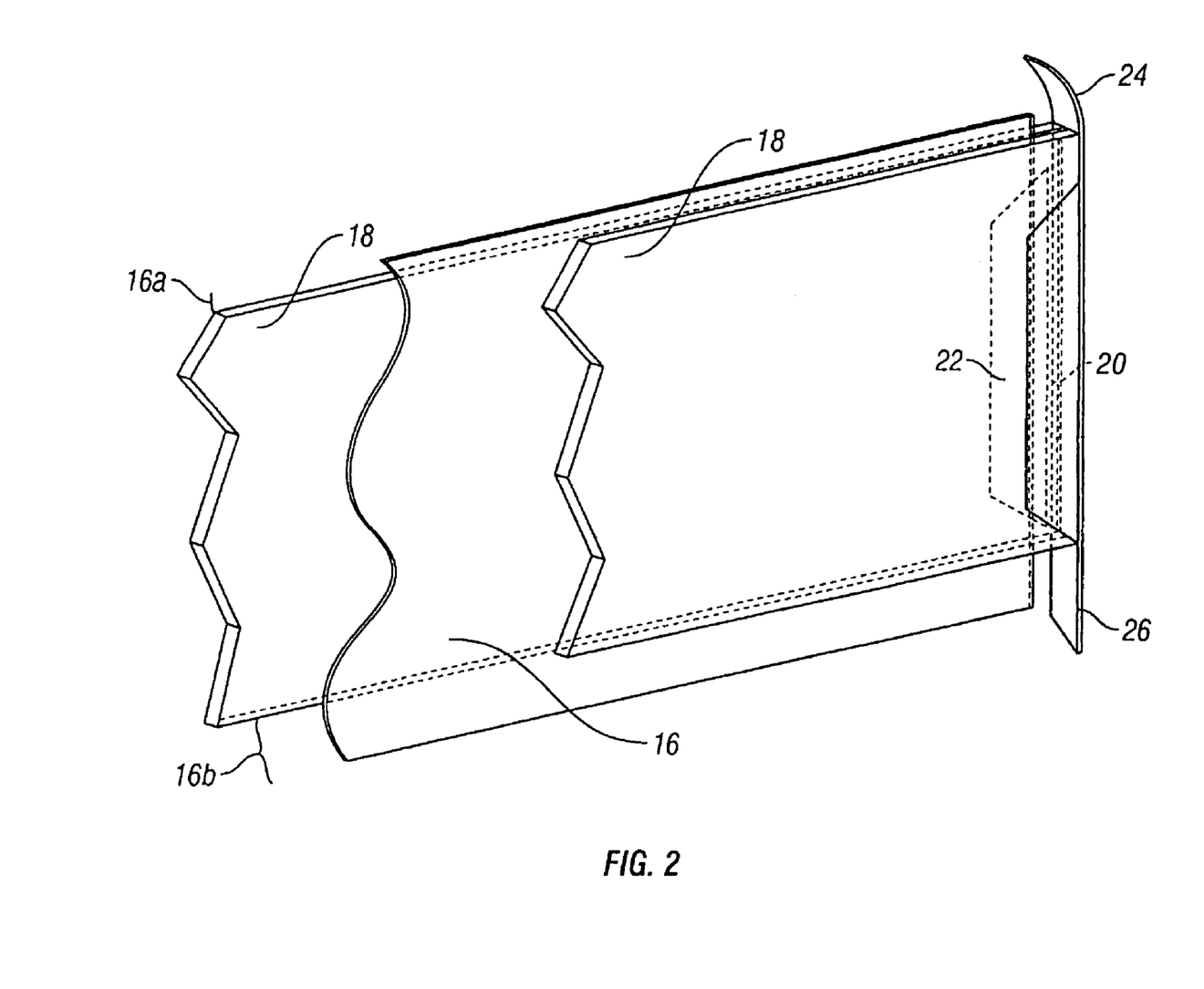
FIG. 2 is a partial perspective view of the wick, the plates, and the clips of the lamp depicted in FIG. 1.

With reference to FIG. 2, the clips 20 (only one of which is shown) are positioned on side edges of the plates. The clips include side flanges 22 that press and support the wick between the plates, and by holding the wick in compression the clips enhance the capillary action of the liquid up the wick. The wick 16 is sized and positioned between the plates such that a top portion 16a extends out of the body of the lamp and a bottom portion 16b extends past the lower edge of the plates and contacts the liquid. In use, the top portion of the wick is lit so that a flame is present across the top portion of the wick conforming to the shape of the wick. In this embodiment, the wick is straight, but it should be appreciated that the wick and the plates can be configured in various shapes. For instance, the wick can be configured, when viewed from the top, in the shape of an arc, circle, square, triangle, heart, alpha-numeric shapes, depending on the particular decorative use.

The material and thickness of the wick 16 are selected primarily to promote prolonged burning and capillary action with the liquid used. It is unnecessary to configure the wick with materials having high heat conductivity, such as stainless steel, aluminum, brass, bronze and the like. The wick can be a single sheet of fiberglass weighing approximately eight ounces when the combustible liquid is a petroleum-based paraffin. In this embodiment, the wick is made of three sheets of fiberglass weighing approximately twenty-four ounces. The wick can also be made of cotton, carbon or any other material capable of prolonged burning and may be dyed into various colors to enhance aesthetic appeal. The top portion of the wick may be bound to avoid fringing of the burning end of the wick. In this embodiment, the top of the wick 16 extends approximately $1/16$ inch to $1/4$ inch above the plates and approximately $1/2$ inch to $3/4$ inch below the plates. The horizontal length of the wick is at least $1/4$ inch narrower than the plates to ensure that the wick does not extend horizontally beyond the plates, which in turn avoids the spreading of flames to the top chamber 14 (FIG. 1). In this embodiment, the wick is preferably less than three inches high in the vertical direction to ensure upward travel of liquid to the top of the wick.

Figure 6:
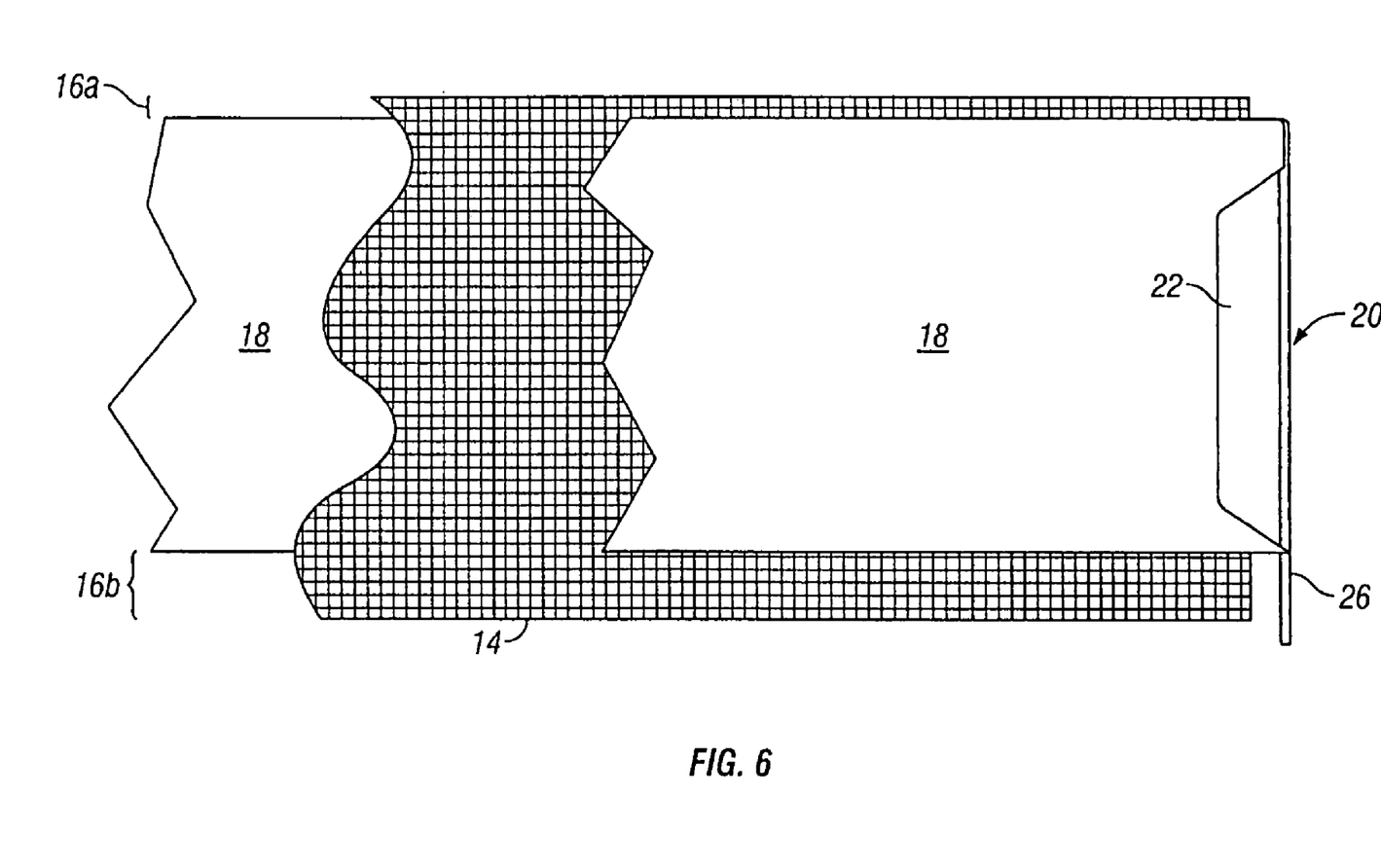
FIG. 6 is a cross-sectional perspective view of a wick, plate and alternate clip configuration for use with an oil lamp in accordance with the present invention.

With continued reference to FIG. 2, the clips 20 have a top portion 24 curved toward the wick 16 so that the flame from the wick heats the clip further includes a bottom portion 26 that extends into the reservoir of liquid. Each clip is made of a conductive material having a relatively high conductivity in comparison to the body 12 of the lamp 10. In this embodiment, each clip has a height of approximately 3.5 inches. The conducting element can be made of stainless steel, aluminum, brass, bronze or any other heat-conducting material. The bottom portion of the clip is positioned to contact the liquid and a shelf 28 (FIG. 1). In other embodiments the clips may not include a top portion (FIG. 6).

With reference to FIGS. 1 and 2, the plates 18 are suspended in the top chamber 14. In this embodiment, the plates 18 are at least $1/8$ inch thick and made of glass or a similar material configured to withstand high temperatures without breaking, cracking or shattering. Each plate has a horizontal length of approximately 12.5 inches, a height of approximately two inches, and a thickness of approximately $1/8$ inch. The plates extend at least $1/4$ inch above a top surface 30 of the lamp 10 to reduce the conduction of heat to the body 12 of the lamp, and the plates do not contact the shelf 28 but rather are suspended at least $1/16$ inch above the shelf using the clips. The top surface may have an indented portion (not shown) to hold scented oil. The plates are suspended above the shelf so that the wick can contact the liquid (not shown). In an alternative the shelf incorporates a device (not shown) that supports the plates some distance above the surface of the shelf, thus requiring no top surface 30 from which to suspend the plates, which in turn may leave the top chamber 14 exposed. Optionally, the plate may be in contact with the shelf.

Figure 3:
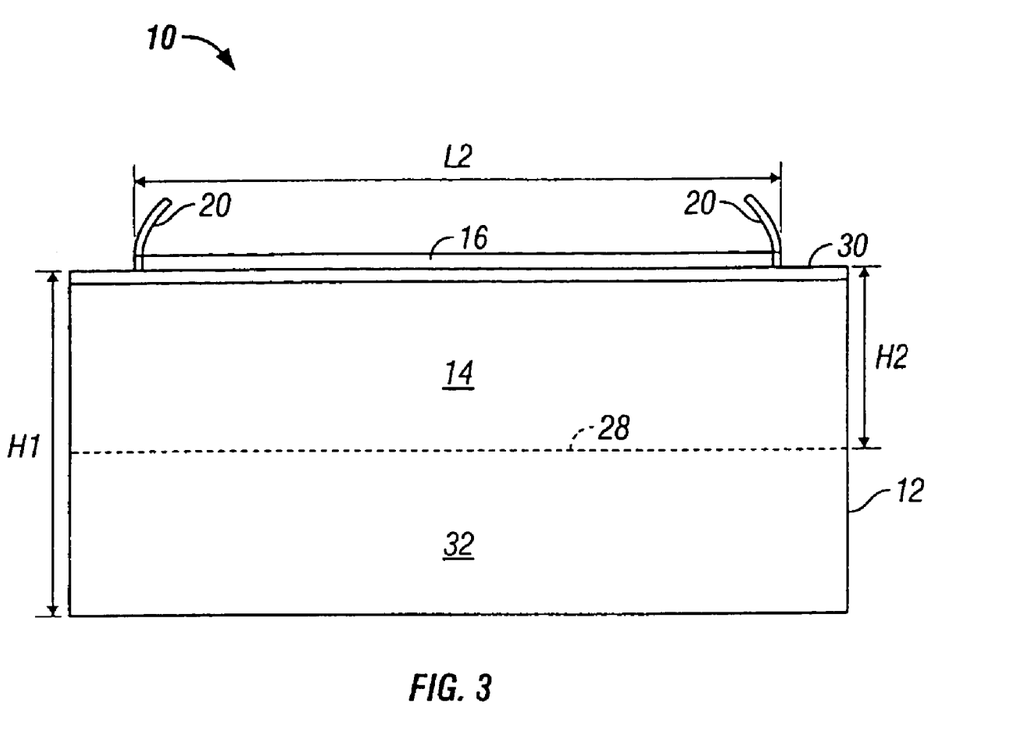
FIG. 3 is a side view of the lamp depicted in FIG. 1.
Figure 4:
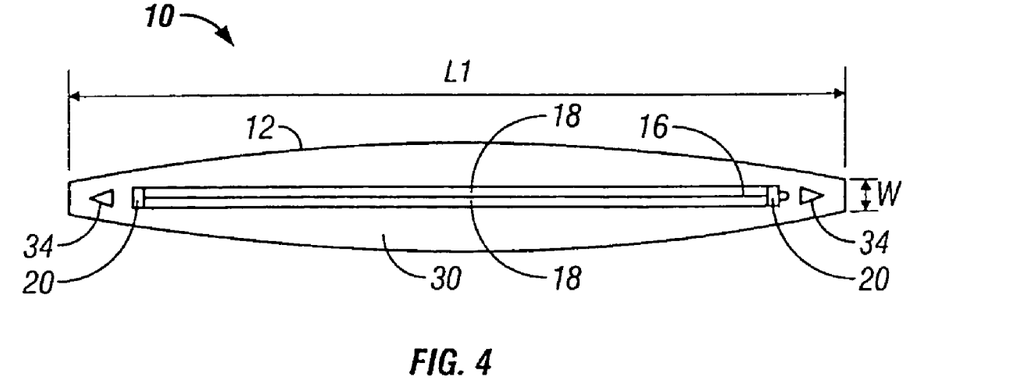
FIG. 4 is a top view of the lamp depicted in FIG. 1.

With reference FIGS. 1, 3 and 4, the body 12 of the lamp is eye shaped and has a height H1, which can be approximately 5.5 inches. However, it should be appreciated that the body of the lamp can be configured in any shape such as a circle, square, rectangle, polygon or curve. The body of the lamp is made from a material having a relatively low conductivity, which may be aluminum, steel, copper, brass, platinum, resin, or any other material. The external body of the lamp may be covered with an external veneer 13, which may include or resemble wood, leather, wax, porcelain, or a similar appearance with aesthetic appeal. The lamp has a length L1, here fifteen inches, and a width W at each end, here one inch, but it should be appreciated that the lamp can come in a plurality of alternative sizes.

Figure 5:
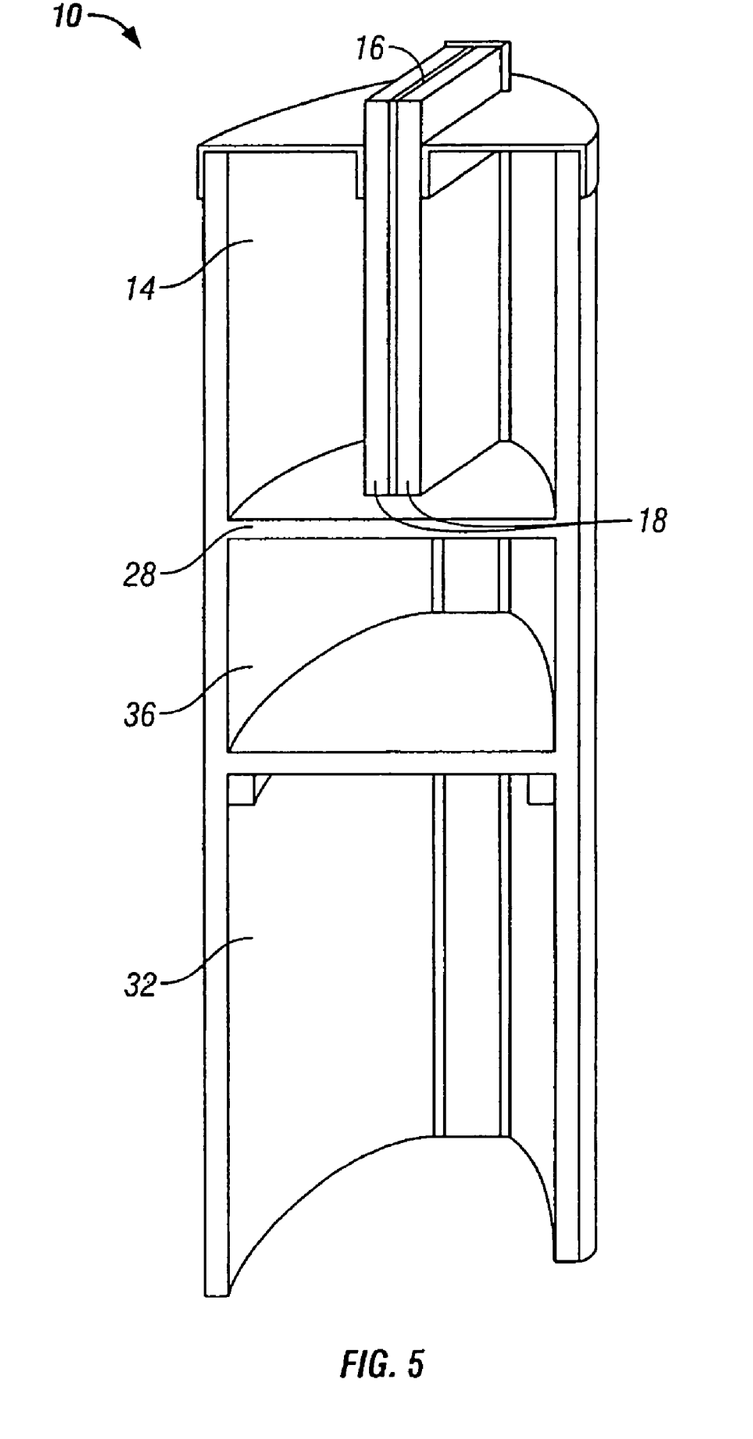
FIG. 5 is a cross-sectional perspective view of a second preferred embodiment lamp having three chambers in vertical alignment.

With continued reference to FIG. 1, the lamp has two chambers, the top chamber 14 and a bottom chamber 32 separated by the shelf 28. The top chamber 14, also referred to as an oil chamber, is configured to hold the liquid. In a preferred embodiment, the liquid is a vegetable based, non-toxic scented oil. Also, the liquid can be a petroleum-based paraffin or any other combustible fuel. The bottom chamber serves as an insulating chamber to reduce the rate at which the liquid loses heat through the shelf to the surface upon which the lamp rests and can be filled with a foam or other material to enhance the insulation. The lamp 10 further includes one or more holes 34 on the top surface 30 of the body 12 to allow for the filling and refilling of a liquid upon depletion. In the preferred embodiment, the holes are located at one or both ends of the horizontal alignment of the wick 16. The holes also promote the release of fragrance to the environment when the lamp contains a scented liquid. Chambers 14, 32 are in vertical alignment. Alternatively, the lamp can be configured to have only one chamber or to have a third chamber, a middle chamber 36 (FIG. 5).

Figure 7:
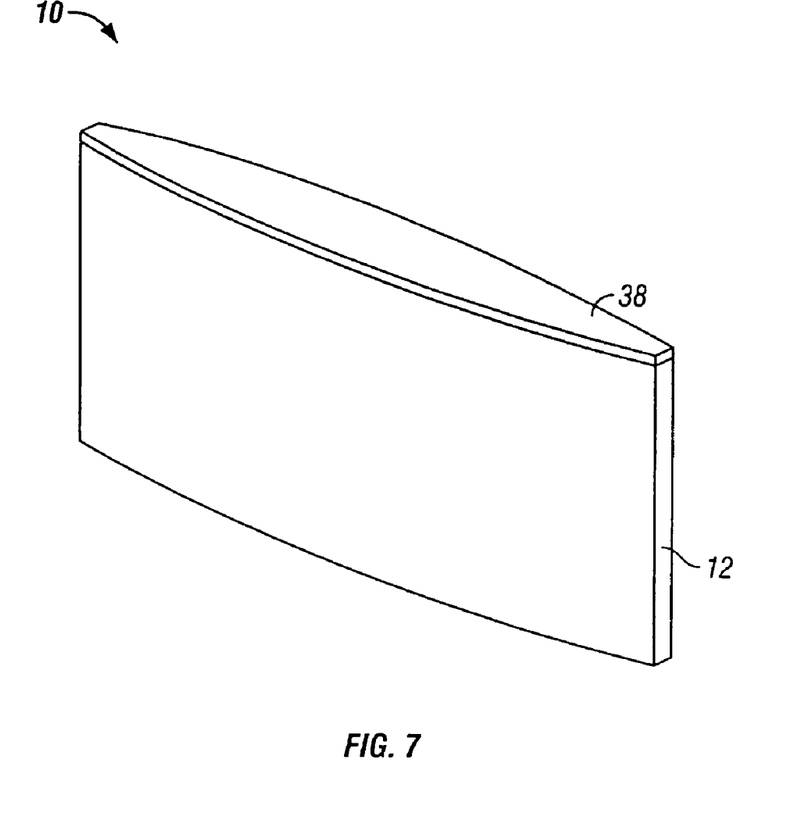
FIG. 7 is a perspective view of the lamp depicted in FIG. 1, incorporating an elongated lid.

With reference to FIG. 7, the lamp 10 is shown further including an elongated lid 38. The lid is configured to extinguish the wick by completely sealing off air to the flame and reservoir. To extinguish the wick, the user places the lid over the body 12. In one embodiment, the lid is configured to be secured to the body.

Figure 8:
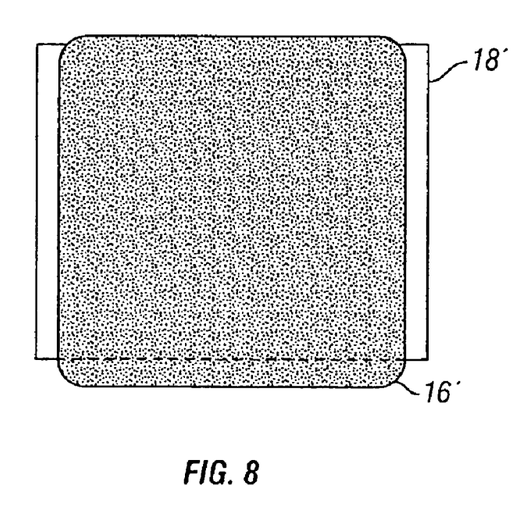
FIG. 8 is a perspective view of a second preferred embodiment of an oil lamp of the present invention, the lamp including an elongated, sheet wick folded about a metal plate.
Figures 9, 11:
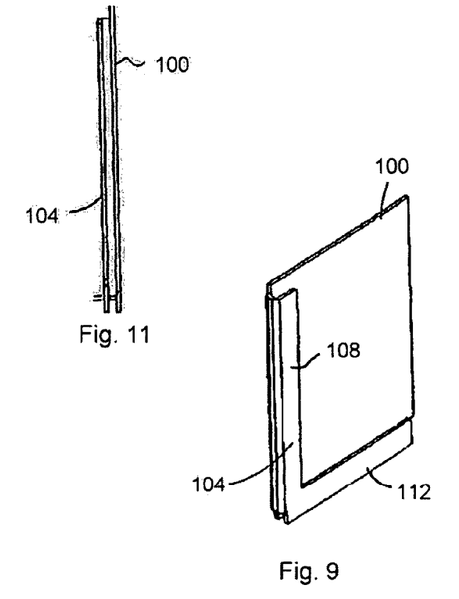
FIG. 9 is a perspective view of an alternative interlocking plate design of the present invention.
FIG. 11 is a end edge elevational view thereof.
Figure 10:
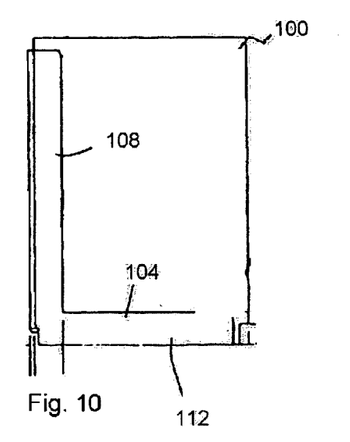
FIG. 10 is a side elevational view thereof.
Figure 12:
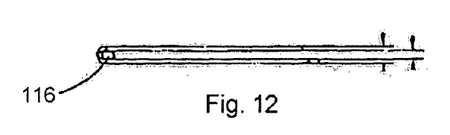
FIG. 12 is a top plan view thereof.

Referring now to FIG. 8, a sheet wick 16' is configured as a sleeve about a rigid plate 18'. The plate is formed of aluminum and may be plated to enhance against erosion. The plate may also be formed of brass, steel, glass or other suitable materials. The wick is wrapped about the plate and stitched in place with a heat-resistant thread such as a fiberglass thread. Preferably, the wick is stretched taut about a plate to further facilitate capillary action.

It should be appreciated from the foregoing description that the present invention provides an oil lamp usable in a variety of decorative applications that has a unique flame formation sustained by improved capillary action, and that has improved means for conducting heat into a scented oil reservoir for enhanced release of fragrance without the need of providing the wick with material having high heat conductivity.

FIGS. 9-12 show an alternative interlocking plate design of the present invention. It is seen therein that the design comprises a first plate 100 having dimensions of approximately 2.91 inches high by 2.11 inches wide and a thickness of 0.04 inch. The second plate 104 is L-shaped with the leg 108 and the arm 112 each being approximately 0.31 inch wide. The L-shaped plate 104 and the rectangular plate 100 can be formed from a single aluminum sheet which is cut and bent to form these two parallel sheets with the connecting hinge 116 shown for example in FIG. 12.

Advantages of the design of FIGS. 9-12 over the previously-described clipped design are that two parts rather than four (two plate and two clips) are used which lowers cost, makes it more stable; locks the wick in place, easier to assemble; and more of a complete piece. The clip would clamp around the fiber wick with the wick extending ⅛-¼ inch above the plates and hang ⅛-¼ inch below the plates to absorb the fuel. The complete wick piece would then be placed between the center walls on the bottom of the chamber or lamp base, keeping the wick in the proper position at all times. That is, the wall unit can be built into the bottom to support the wick, instead of hanging from the top. By having it secured at the bottom a user can fill the lamp without touching the wick. This is easier, safer and cleaner.

Figure 13:
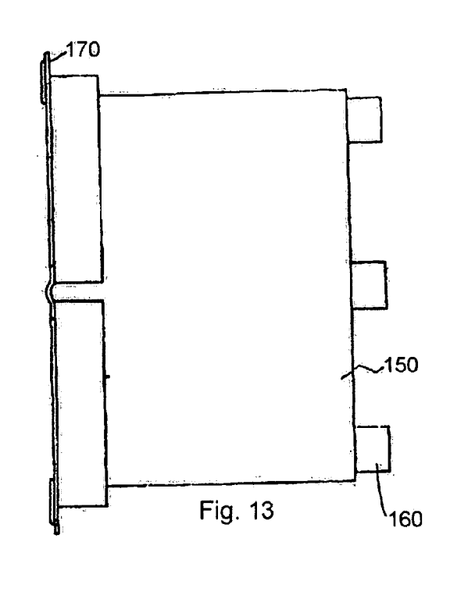
FIG. 13 is a side elevational view of an oil chamber or a fluid chamber of the present invention.
Figure 14:
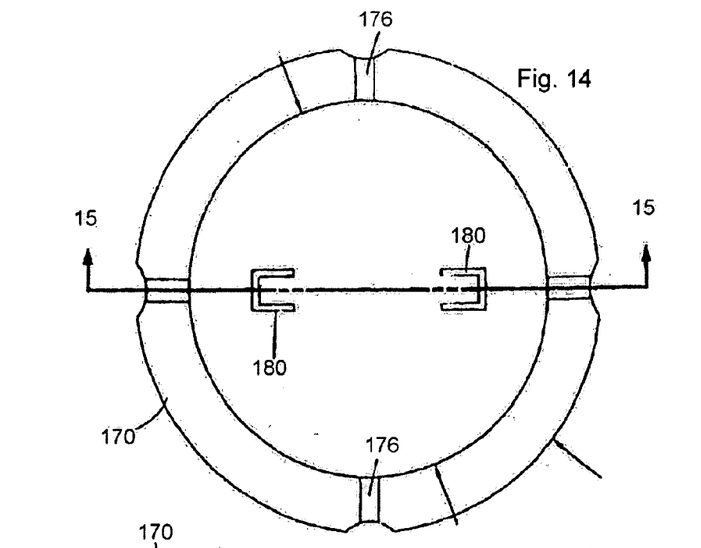
FIG. 14 is a top plan view thereof.
Figure 15:
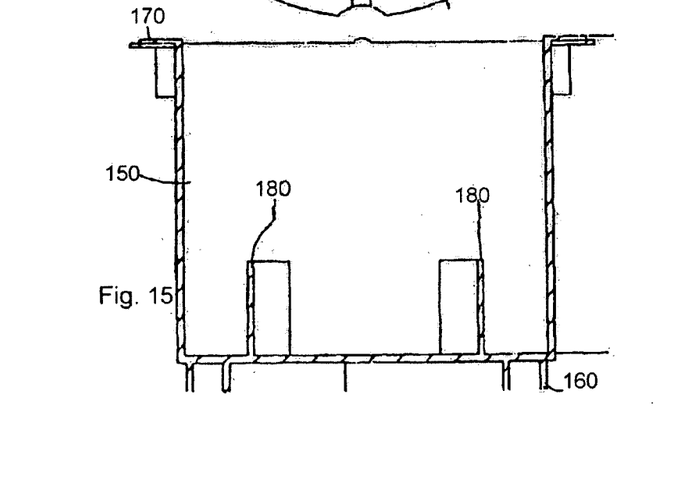
FIG. 15 is a cross-sectional view.

FIGS. 13-15 show an oil chamber or a fluid chamber 150 of the present invention having legs 160 as shown in FIG. 13 to provide air flow, reducing heat to the base material. The chamber can be made, for example, of polyethylene, metal or ceramic. A ledge 170 shown in FIG. 14 for example, protects the base material from heat and fuel spillage. Air holes 176, as similarly shown in FIG. 14, for example, are provided to release heat and fragrance. As shown in FIGS. 14 and 15, a pair of spaced built-in walls 180 center and keep the wick upright. If glass or ceramic plates are used the wick is around ¼ inch thick; if metal sheets are used, it is approximately ⅛ inch thick. Although the walls in the drawing figures are designed for glass or ceramic, a preferred embodiment is to use metal due to the durable qualities of metal, cost and the metal enhances the fragrance emission.

Figure 16:
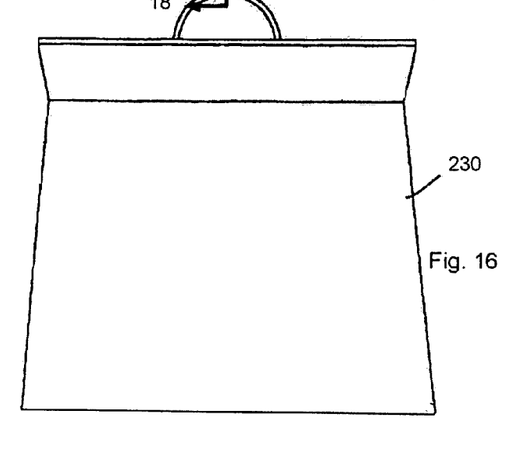
FIG. 16 is a side-elevational view of a solid mineral wick chamber assembly of the present invention.
Figure 17:
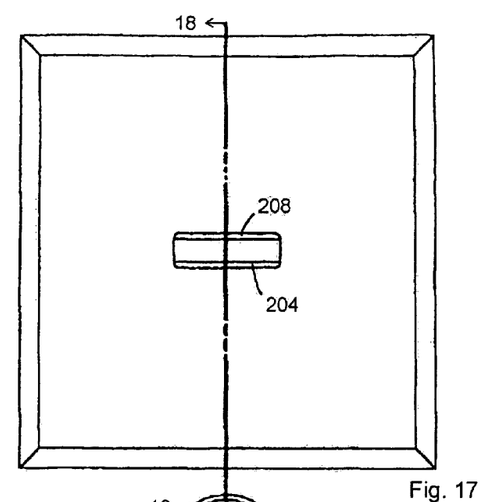
FIG. 17 is a top plan view thereof.
Figure 18:
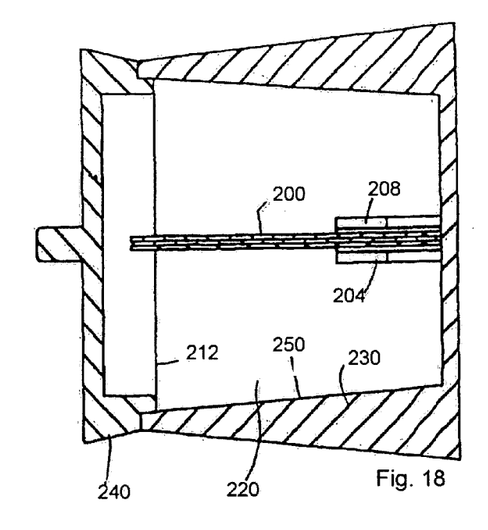
FIG. 18 is a cross-sectional view taken on line 18-18 of FIG. 17.

A solid mineral wick assembly is shown in FIGS. 16-18. The freestanding solid mineral wick 200 is best shown in FIG. 18. Plates 204, 208 are built-in to hold the wick upright. A top plate 212 protects the fluid in the chamber 220 formed by the base 230. The base is made of wood, metal, ceramic glass, plastic or the like. A built-in snuffer 240 is shown at the top of the figures. Element 250 is an inner chamber made of ceramic, glass, metal or polymers. The wick material can be a very porous material such as sandstone and limestone with a vertical capillary flow. It preferably is cut to size from an existing rock formation. The wick can have a thickness of ⅛-½ (preferably ¼) inch and width of ½ to 10 inches depending on the size of the oil or fragrance lamp.

Figure 19:
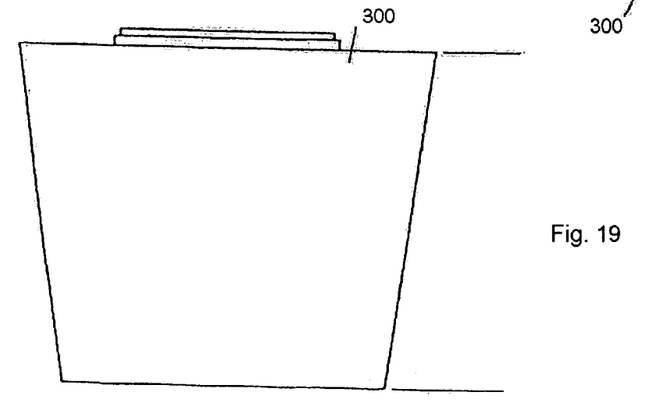
FIG. 19 is an alternative of the assembly of FIG. 16.
Figure 20:
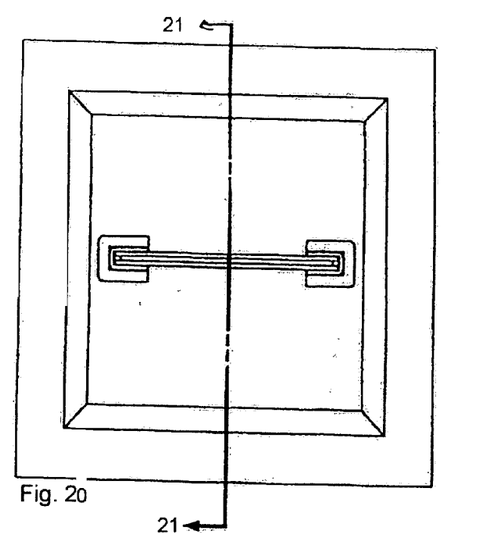
FIG. 20 is a top plan view thereof.
Figure 21:
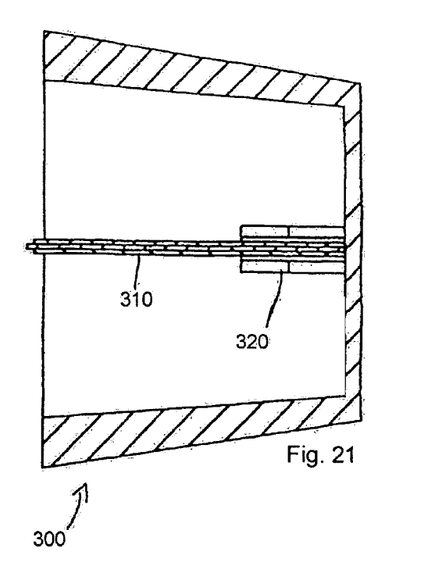
FIG. 21 is a cross-sectional view taken on line 21-21 of FIG. 20.

An alternative solid mineral wick assembly is shown in FIGS. 19-21 at 300. It can have height dimensions as can be understood from FIG. 19 of 3.00 inches and a width dimension as understood from FIGS. 20 and 21 of 3.90 inches at the top. It similarly includes the solid mineral wick 310 and plates 320 for holding the wick upright.

Figure 22:
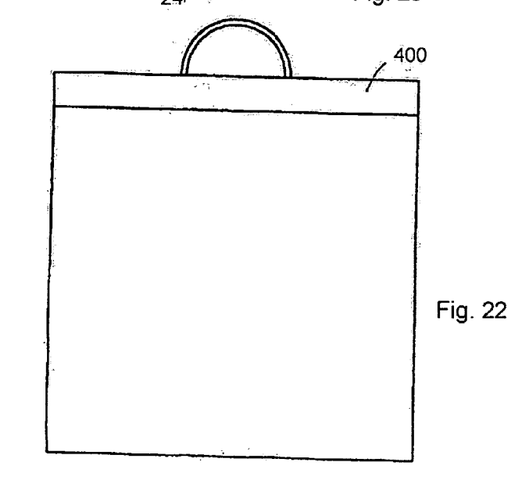
FIG. 22 is another alternative assembly of the present invention.
Figure 23:
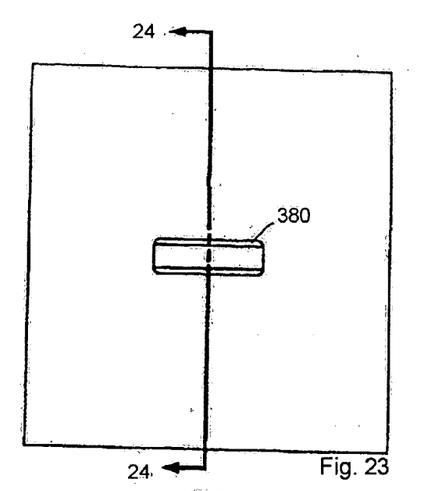
FIG. 23 is a top plan view thereof.
Figure 24:
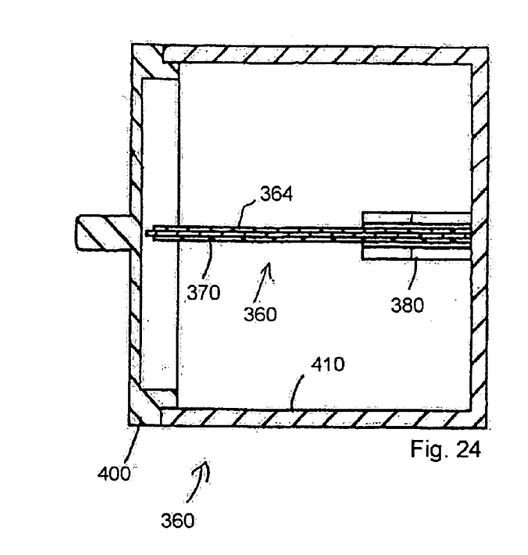
FIG. 24 is a cross-sectional view taken on line 24-24 of FIG. 23.

A further solid mineral wick with fiber material invention embodiment is shown in FIGS. 22-24 at 360. A solid mineral material 364 is shown in FIG. 24 surrounding a fiber material core 370. The centering plates 380 hold it centered and upright within the base. An inner chamber 390 is formed in the base, and a snuffer 400 is provided for extinguishing the flame. The snuffer 400 has a heat resistant top. The wick layers as illustrated in the drawings show the fibers that will be intertwined in the stone material. The fibers flow vertically and can be made out of inorganic materials such as fiberglass or graphite. The stone can be a permeable clay-like mineral blend that is resistant to high heat and flames. To form the wick the fiber material can be positioned vertically in a mold and a liquid clay can be poured into the mold to form a thin sheet (approximately ¼ inch thick) and the width would be ½ inch to 10 inches depending on the size of the oil lamp. Element 410 is an additional chamber if the base is made out of a flammable, non heat resistant material (e.g. wood, plastic, cardboard), otherwise it is the inner side of the base which would be made out of heat and flame resistant materials (e.g., metal, glass, ceramic).

Figure 25:
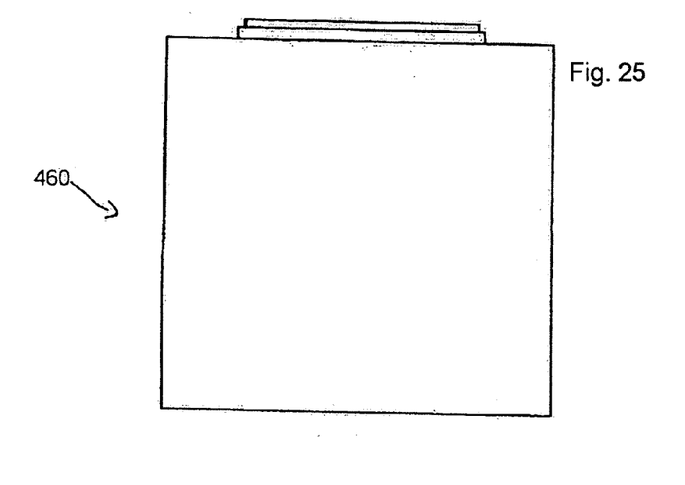
FIG. 25 is a side elevational view of an alternative chamber of the present invention.
Figure 26:
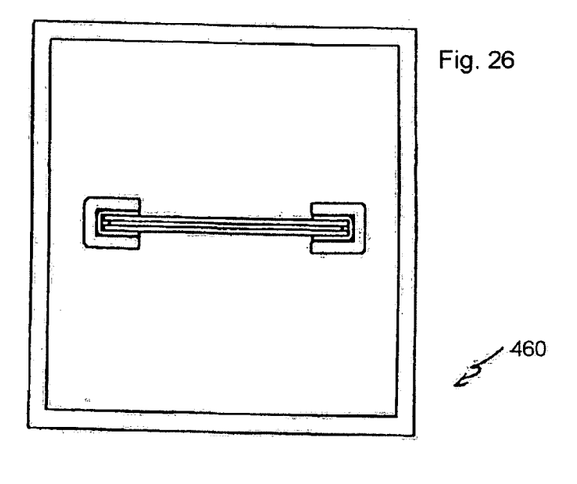
FIG. 26 is a top plan view thereof.

An alternative assembly design is similar to FIGS. 19-21 is shown in FIGS. 25 and 26 at 460. It can have referring to FIG. 25, a width dimension of 3.30 inches and a height dimension of 3.00 inches.

In summary, an oil lamp for providing a unique flame formation usable in a variety of decorative applications is disclosed herein. The lamp includes a body that has an open upper end and that defines a chamber for carrying a combustible liquid. The lamp further includes a sheet wick having a lower end located in the chamber of the body, for contacting the combustible liquid, and an upper end projecting upwardly from the open upper end. The wick may be positioned between first and second plates arranged in a spaced, confronting relationship to enhance capillary action or may be wrapped about a rigid plate. When lit, the lamp provides a unique flame formation. Optionally, the lamp may include scented oil and a conductive element to promote the release of fragrance upon heating, and the wick can be configured free of material having a high heat conductivity.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. However, it is intended that all such variations not departing from the spirit of the invention be considered as within the scope thereof.

We claim:

1. An apparatus comprising:
   a body defining a chamber for carrying a combustible liquid and having an open upper end;
   first and second plates arranged in a spaced, confronting relationship with lower portions located within the chamber of the body;
   the first plate is a planar sheet and has substantially more surface area than the second plate;
   the second horizontal plate has a first vertical leg and a second leg; the first leg is aligned with respect to the second leg:
   the first plate is joined to the second plate along an outer edge of the first leg of the second plate:
   a sheet wick, which has a lower end located in the chamber of the body for contacting the combustible liquid, is sandwiched between the first plate and the first leg and the second leg of the second plate;
   the sheet wick is free of material having a high heat conductivity; and
   the sheet wick has an upper end, which projects upwardly from the first plate and the first leg of the second plate.

2. The apparatus of claim 1 wherein the plates are rectangular or square.

3. The apparatus of claim 1 wherein the plates are made of metal, ceramic or plastic.

4. The apparatus of claim 1 wherein the plates display a design, decoration or color on a flat side of the first plate.

5. The apparatus of claim 1 wherein the wick has a core lining or stiffing agent.

6. The apparatus of claim 1 wherein the wick is a rigid, sheet wick.

7. The apparatus of claim 1 further comprising a plurality of clips positioned on side edges of the first and second plates to sandwich the sheet wick between the plates.

8. The apparatus of claim 7 wherein at least one of the clips has a top portion extending above and curved over the upper portion of the wick, side flanges configured to hold the first and second plates and the wick together, and a bottom portion positioned in the chamber of the body.

9. The apparatus of claim 1 wherein the first and second plates are configured to hold the wick such that the upper portion of the wick forms a selected decorative shape as viewed from above.

10. The apparatus of claim 1 wherein the selected decorative shape is selected from a group consisting of line, arc, circle, square, triangle, heart, and alpha-numeric shapes.

11. The apparatus of claim 1 wherein the combustible liquid includes a fragrance.

12. The apparatus of claim 1 wherein the combustible liquid includes an air purifring fuel.

13. The apparatus of claim 1 wherein the wick is made of an inorganic fibrous material.

* * * * *